United States Patent [19] [11] 4,406,910
Pilgram et al. [45] Sep. 27, 1983

[54] PESTICIDAL 3-(2,3-DIHYDRO-2-ALKYLBENZOFURAN-7-YL)-5-(R-OXY)-1,3,4-OXADIAZOL-2(3H)-ONES

[75] Inventors: Kurt H. Pilgram; Richard D. Skiles, both of Modesto, Calif.

[73] Assignee: Shell Oil Company, Houston, Tex.

[21] Appl. No.: 375,438

[22] Filed: May 6, 1982

Related U.S. Application Data

[63] Continuation-in-part of Ser. No. 273,833, Jun. 15, 1981, abandoned, which is a continuation-in-part of Ser. No. 187,234, Sep. 15, 1980, abandoned.

[51] Int. Cl.$^3$ .................. A01N 43/82; C07D 271/10
[52] U.S. Cl. ...................... 424/272; 548/144; 549/469
[58] Field of Search ................ 548/144; 424/272

[56] References Cited

U.S. PATENT DOCUMENTS 4,302,592 11/1981 Tieman ............... 548/144

Primary Examiner—Alton D. Rollins

[57] ABSTRACT

Pesticidal 3-(2,3-dihydro-2-alkylbenzofuran-7-yl)-5-(R-oxy)-1,3,4-oxadiazol-2(3H)-ones.

5 Claims, No Drawings

PESTICIDAL 3-(2,3-DIHYDRO-2-ALKYLBENZOFURAN-7-YL)-5-(R-OXY)-1,3,4-OXADIAZOL-2(3H)-ONES

This application is a continuation-in-part of Application Ser. No. 273,833, filed June 15, 1981, abandoned, a continuation-in-part of Application Ser. No. 187,243, filed Sept. 15, 1980, abandoned.

DESCRIPTION OF THE INVENTION

It has been found that certain 3-(2,3-dihydro-2-alkylbenzofuran-7-yl)-5-(R-oxy)-1,3,4-oxadiazol-2(3H)-ones of the formula

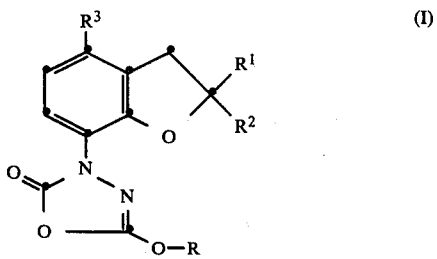

wherein R is alkyl of one or two carbon atoms or is 2-propynyl, $R^1$ is hydrogen or alkyl of 1 to 3 carbon atoms, $R^2$ is alkyl of 1 to 3 carbon atoms, and $R^3$ is hydrogen, middle halogen or alkyl of 1 to 3 carbon atoms, possess useful pesticidal properties.

By "middle halogen" is meant the elements bromine and chlorine. Each alkyl moiety suitably is of straight-chain or branched-chain configuration. Preferably, each alkyl moiety is methyl. The highest pesticidal activity appears to be associated with the subgenus wherein $R^1$ and $R^2$ each is methyl, and $R^3$ is hydrogen, the individual species of that subgenus wherein R is methyl having the highest activity.

The compounds of the invention wherein $R^1$ is hydrogen and $R^2$ is methyl exist in the form of optical isomers. The isomers have not been separated and isolated. This invention contemplates all of the insecticidally active isomers, as well as mixtures containing them.

Compounds of Formula I have been prepared as described in the following examples. In each case, the identity of each precursor, and of each product, was confirmed by appropriate chemical and spectral analyses.

EXAMPLE 1

3-(2,3-dihydro-2,2-Dimethylbenzofuran-7-yl)-5-methoxy-1,3,4-oxadiazol-2(3)-one (1)

3 g of a commercial 10% palladium-on-charcoal catalyst was added to a solution of 82.2 g of 2,3-dihydro-2,2-dimethyl-7-nitrobenzofuran (prepared by the method described in U.S. Pat. No. 3,412,110) in 500 ml of tetrahydrofuran. The resulting mixture was treated with hydrogen (50 p.s.i.g.) in a Parr shaker, then filtered. The solvent was evaporated from the filtrate, and the residue was dissolved in one liter of anhydrous ether cooled to 0° C. The solution was treated with a slight excess of gaseous anhydrous hydrogen chloride. The resulting mixture was filtered and the solid was dried to give 7-amino-2,3-dihydro-2,2-dimethylbenzofuran hydrochloride (1A), as a white solid.

A chilled (5° C.) solution of 82.7 g of 1A, 146 ml of concentrated hydrochloric acid and 450 ml of water was diazotized by the drop-by-drop addition over a 30-minute period of a solution of 31.5 g sodium nitrite in 45 ml of water. After filtration, the filtrate was stirred at 5° C. for 45 minutes, and then added drop-by-drop to a stirred solution of 367 g of sodium sulfite in 705 ml of water, at 5° C. The resulting mixture was stirred for 2 hours at room temperature. Then a slurry of 72.2 g of sodium dithionite in 100 ml of water was added in portions. The resulting mixture was stirred for 2 hours at room temperature, then heated at 70° C. for 10 minutes, and 500 g of potassium chloride was added. After 18 hours, the resulting mixture was cooled to 5° C. and filtered. The solid was dried to give the potassium salt of (2,3-dihydro-2,2-dimethylbenzofuran-7-yl)hydrazinesulfonic acid (1B), as an off-white solid, m.p.: approximately 120° C. (with decomposition).

18 g of hydrogen chloride was introduced into a stirred slurry of 56 g of (1B) in 250 ml of ethanol. The resulting mixture was stirred for 3 hours, and the solvent was evaporated. The residue was dissolved in 50 ml of water, the solution was made basic with aqueous sodium hydroxide, and extracted with ether. The extract was washed with cold water, dried (MgSO$_4$), and filtered, and the solvent was evaporated to give 2,3-dihydro-2,2-dimethyl-7-hydrazinobenzofuran (1C) as a dark oil.

17.8 g of (1C) thus prepared and 12.9 g of ethyldiisopropylamine were dissolved in 200 ml of tetrahydrofuran. 9.45 g of methyl chloroformate was added drop-by-drop to the stirred solution, and the resulting mixture was stirred for one hour. The solvent then was evaporated, the residue was washed with water and extracted with ether, and the extract was dried. Part of the ether was evaporated from the extract and the remaining solution was cooled. The resulting solid was collected to give the methyl ester of 2-(2,3-dihydro-2,2-dimethylbenzofuran-7-yl)hydrazinecarboxylic acid (1D), as a white solid, m.p.; 101°–102° C.

A solution of 6.3 g of phosgene in 60 ml of benzene was added to a solution of 13.5 g of (1D) in 100 ml benzene at room temperature. The resulting mixture was held for 24 hours at room temperature, and the solvent was evaporated to give the methyl ester of 2-(2-chlorocarbonyl)-2-(2,3-dihydro-2,2-dimethylbenzofuran-7-yl)hydrazinecarboxylic acid (1E), as a white crystalline solid, m.p.: 118°–120° C.

A solution of 13 g of 1E and 15 g of ethyldiisopropylamine in 200 ml of methanol was refluxed for 15 minutes. After cooling, the solvent was evaporated. The residue was triturated with water, acidified with hydrochloric acid and extracted with ether. The extract was dried (MgSO$_4$) and the solvent was evaporated. The residue was crystallized from ether-hexane to give 1, as a white solid, m.p.: 52°–54° C.

EXAMPLES 2, 3, 4 AND 5

By the procedures described in Example 1:

3-(2,3-dihydro-2,2-dimethylbenzofuran-7-yl)-5-ethoxy-1,3,4-oxadiazol-2(3H)-one (2) was prepared, as an oil, from the ethyl ester of 2-(2-chlorocarbonyl)-2-(2,3-dihydro-2,2-dimethylbenzofuran-7-yl)hydrazinecarboxylic acid (2E), a solid, m.p.: 113°–115°;

3-(2,3-dihydro-2,2-dimethylbenzofuran-7-yl)-5-(2-propynyloxy)-1,3,4-oxadiazol-2(3H)-one (3), was prepared, as a solid, m.p.: 72°–74° C., from the 2-propynyl ester of 2-(2-chlorocarbonyl)-2-(2,3-dihydro-2,2-dimethylbenzofuran-7-yl)hydrazinecarboxylic acid (3E), an oil;

3-(2,3-dihydro-2,2,4-trimethylbenzofuran-7-yl)-5-methoxy-1,3,4-oxadiazol-2(3H)-one (4) was prepared, as a solid, m.p.: 60°-62°, from the methyl ester of 2-(2-chlorocarbonyl)-2-(2,3-dihydro-2,2,4-trimethylbenzofuran-7-yl)hydrazinecarboxylic acid, (4E), an oil;

3(2,3-dihydro-2-methylbenzofuran-7-yl)5-methoxy-1,3,4-oxadiazol-2(3H)-one (5), was prepared as a solid, m.p.: 79°-81°, from the methyl ester of 2-(2-chlorocarbonyl)-2-(2,3-dihydro-2-methylbenzofuran-7-yl)hydrazinecarboxylic acid (5E), an oil.

Compounds of the invention containing the following moieties can be prepared in a similar manner:

| R | R$^1$ | R$^2$ | R$^3$ |
|---|---|---|---|
| methyl | methyl | methyl | isopropyl |
| methyl | H | ethyl | H |
| methyl | ethyl | ethyl | ethyl |
| methyl | H | ethyl | H |
| methyl | H | isopropyl | H |

Compounds of the invention wherein R$^3$ is middle halogen are prepared in the same manner from the appropriate hydrazinecarboxylic acid ester substituted at the 4-position of the benzofuranyl moiety by the halogen.

Activity of compounds of this invention with respect to insect and acarine pests was determined by using standardized test methods to measure the toxicity of the compounds as follows:

I. Houseflies (*Musca domestica* (Linne)) were tested by placing 50 4- to 5-day old houseflies into a spray cage and spraying with 0.6 ml of a solution of test compound. After spraying, the flies were anesthetized with CO$_2$ and transferred to a recovery cage containing a milk pad for food. The cages were held for 18-20 hours after which mortality counts were made. Both dead and moribund flies were counted. The tests were conducted employing several different dosage rates for each test compound.

II. Pea aphids (*Acyrthosiphon pisum* (Harris)) were tested by placing about 100 aphids on broad bean plants. The plants were sprayed with dilutions of an acetone solution of the test compound in water containing an emulsifier and held in containers under laboratory conditions for 18 to 20 hours, at which time the living aphids in the containers were counted. The tests were conducted employing several different dosage rates for each test compound.

III. Adult female two-spotted spider mites (*Tetranychus urticae* (Koch)) were tested by placing 50-75 mites on the bottom side of leaves of pinto bean plants. The leaves were sprayed with dilutions of an acetone solution of the test compound in water containing an emulsifier and kept under laboratory conditions for about 20 hours, at which time mortality counts were made. The tests were conducted employing several different dosage rates for each test compound.

IV. Mosquito larvae (*Anopheles albimanus* (Weide)) were tested by placing 10 living and active mosquito larvae in a jar containing a 0.1 ml aliquot of a 1% acetone solution of the test compound thoroughly mixed with 100 ml of distilled water. After 18-22 hours, mortality counts were taken. Both dead and moribund larvae were counted as dead. Larvae which did not swim after being prodded with a needle were considered moribund. The tests were conducted employing several different dosage rates for each compound.

V. Corn earworm larvae (*Heliothis zea* (Boddie)) were tested by spraying a broad bean plant with dilutions of an acetone solution of the test compound in water containing an emulsifier. Immediately after spraying, 5 larvae were transferred to the plant and held for 44-46 hours, at which time the dead and moribund larvae were counted. The tests were conducted employing several different dosage rates for each test compound.

In the case of each species of the insect, the concentration of the test compound by weight in the formulation required to kill fifty percent of the test insects—i.e., the LC$_{50}$ dosage—was determined. The results are set out in Table I.

TABLE I

| Compound Number | LC$_{50}$ % w | | | | Mosquito Larvae |
|---|---|---|---|---|---|
| | House-fly | Pea Aphid | Corn Earworm | Spider mite | |
| 1 | 0.005 | 0.00003 | 0.0218 | 0.03 | 0.006 (ppm) |
| 2 | 0.03 | 0.00009 | 0.1 | 0.2 | >0.1 (ppm) |
| 3 | 0.019 | 0.00015 | 0.078 | 0.031 | >0.1 (ppm) |
| 4 | 0.02 | 0.00003 | 0.024 | 0.035 | 0.01 (ppm) |
| 5 | 0.016 | 0.0001 | 0.029 | 0.064 | 0.027 (ppm) |

Compounds of the invention can be used to control pests at a locus to be protected by applying to that locus a suitable pesticidal composition containing the compound of the invention. The composition comprises an adjuvant—that is, a carrier, optionally a surface-active agent—and, as active ingredient, a pesticidal compound of Formula I. Likewise, the invention includes also a method of combatting insect pests at a locus which comprises applying to the locus an effective amount of a pesticidal compound of Formula I.

The term "carrier" as used herein means a solid or fluid material, which may be inorganic or organic and of snythetic or natural origin, with which the active compound is mixed or formulated to facilitate its application to the plant to be treated, or its storage, transport or handling.

Suitable solid carriers are natural and synthetic clays and silicates, for example, natural silicas such as diatomaceous earths; magnesium silicates, for example talcs, magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate, also are contemplated. The said emulsions may be of the water-in-oil or the oil-in-water type, and may have a thick mayonnaise-like consistency.

The compositions may also contain other ingredients, for example, other compounds possessing pesticidal, especially insecticidal, acaricidal, herbicidal or fungicidal properties.

The method of applying the pesticidal compound to control pests comprises applying it, ordinarily in a composition of one of the aforementioned types, to a locus to be protected from the pests, such as the foliage and/or the fruit of plants. It is of course applied in an amount sufficient to exert the desired action. This dosage is dependent upon many factors, including the carrier employed, the method and conditions of the application, whether the formulation is present at the locus in the form of an aerosol, or as a film, or as discrete particles, the thickness of film or size of particles, and the like, proper consideration and resolution of these factors to provide the necessary dosage of active material at the locus to be protected being within the skill of those versed in the art. In general, however, the effective dosage of the pesticidal compound at the locus to be protected—i.e., the dosage which the pests contact—is of the order of 0.001 to 0.05% based on the total weight of the formulation, though under some circumstances the effective concentration will be as little as 0.0001% or as much as 2%, on the same basis.

I claim as my invention:

1. A compound of the formula:

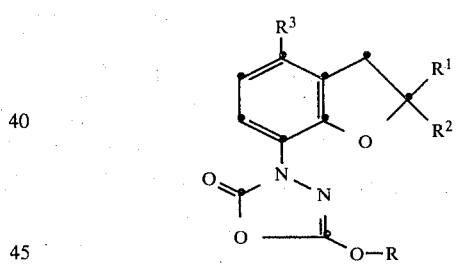

wherein R is alkyl of one or two carbon atoms or is 2-propynyl, $R^1$ is hydrogen or alkyl of 1 to 3 carbon atoms, $R^2$ is alkyl of 1 to 3 carbon atoms, and $R^3$ is hydrogen, middle halogen or alkyl of 1 to 3 carbon atoms.

2. A method for controlling insect and acarine pests which comprises applying to the locus to be protected an effective dosage of a compound of claim 1.

3. A pesticidal composition comprising a compound of claim 1 together with an adjuvant therefor.

4. A compound according to claim 1 wherein $R^1$ and $R^2$ each is methyl and $R^3$ is hydrogen.

5. A compound according to claim 4 wherein R is methyl.

* * * * *